United States Patent [19]

Sugo

[11] Patent Number: 5,076,467
[45] Date of Patent: Dec. 31, 1991

[54] DENTAL WASHER
[75] Inventor: Akihiro Sugo, Tokyo, Japan
[73] Assignee: G-C Dental Industrial Corp., Tokyo, Japan
[21] Appl. No.: 521,358
[22] Filed: May 10, 1990
[30] Foreign Application Priority Data
 Jun. 2, 1989 [JP] Japan .................................. 1-139166
[51] Int. Cl.⁵ ................................................ B67D 5/00
[52] U.S. Cl. ........................................ 222/3; 222/54;
 222/65; 222/67; 222/146.5; 392/324
[58] Field of Search ...................... 222/3, 4, 54, 65–69,
 222/146.1–146.5; 137/202; 392/329, 333, 326, 325

[56] References Cited
U.S. PATENT DOCUMENTS

| Re. 18,993 | 11/1933 | Field | 392/324 X |
|---|---|---|---|
| 3,665,156 | 5/1972 | Lee | 137/202 X |
| 3,749,092 | 7/1973 | Williams | 392/333 X |
| 3,786,829 | 1/1974 | Nordo et al. | 137/202 |
| 4,274,553 | 6/1981 | Evers et al. | 222/146.5 |
| 4,327,459 | 5/1982 | Gilbert | 392/333 X |
| 4,370,543 | 1/1983 | Nemeth | 392/324 X |
| 4,675,505 | 6/1987 | Fischer | 392/326 |
| 4,836,145 | 6/1989 | Ronchi | 222/146.5 X |

FOREIGN PATENT DOCUMENTS 197692 8/1980 Japan .
201521 8/1988 Japan .

Primary Examiner—Michael S. Huppert
Assistant Examiner—Kenneth DeRosa
Attorney, Agent, or Firm—Oblon, Spivak, McClelland, Maier & Neustadt

[57] ABSTRACT

A dental washer includes a heating vessel for heating a washing liquid by an electrical heater to generate superheated steam, so electromagnetic pump on a water supply pipe communicating with the heating vessel and a water source, an electromagnetic valve in a steam pipe having at its one end a nozzle for outputting steam and communicating with the nozzle and a superheated steam-filling region of the heating vessel and a level detector for detecting the level of the washing liquid in the heating vessel to turn the electrical heater on when the level reaches the preset upper limit and turn it off when the level reaches the preset lower limit. The dental washer further includes an initial valve-opening circuit energized upon a main switch turned on to hold the electromagnetic valve open, a valve-closing circuit for holding the electromagnetic valve closed in response to a signal from the level detector when the level of the washing liquid in the heating vessel reaches the preset upper limit and keeping it closed, and a manual valve-controlling switch for steam which holds open or closed the electromagnetic valve held closed by the valve-closing circuit.

6 Claims, 3 Drawing Sheets

DENTAL WASHER

BACKGROUND OF THE INVENTION

1. Field of the Invention

The present invention relates to a washer assembly for dental operations, which is designed to jet steam or boiling water so as to clean gypsum models of wax and stains deposited on their surfaces, wash metal frames prior to the placing of porcelanous materials, clean polishing tools of cuttings for clogging-preventing purposes, and so on.

2. Prior Art

In dental operations, washing should frequently be carried out. For instance, when dental prostheses are made on the basis of a prepared gypsum model, it is divided into denture molds by a saw, trimmed by a polishing tool or knife, marked by a color pencil or waxed up, so that it may be stained on its surface with gypsum powders, wax or dirt from the hands of an operator. Such a gypsum model should be washed out to clean its surface of stains. Prior to the placing of porcelanous materials, metal frames also have to be washed out to clean their surface of foreign matter for the purpose of bettering their adhesion to porcelanous materials. Similarly, polishing tools such as carbide bars or diamond points used to polish gypsum models, sintered porcelanous materials or waxes should be washed out to remove cuttings from them for clogging-preventing purposes.

For such washing, dental washers were used, which are of such a structure as set forth in Japanese Utility Model Laid-Open Nos. 197692/1988 and 201521/1988, wherein a washing liquid is heated in a heating vessel by an electrical heater to generate superheated steam and jet it through a gas/liquid separator. In such dental washers, the means for feeding the washing liquid into the heating vessel is provided by an electromagnetic pump of a structure in which first and second pump chambers are located between a suction inlet and a discharge outlet, valves are located on the suction sides of the pump chambers, the valves being normally engaged by springs to inhibit the suction of the washing liquid, and a plunger is passed into the first pump chamber to vary its volume by the magnetic force of an exciting coil. In the electromagnetic pump of such a structure, as the plunger is actuated by the magnetic force of the exciting coil to increase the volume of the first pump chamber, a negative pressure is generated in the first pump chamber to open the valve on its suction side and, hence, suck in the washing liquid. Then, as the plunger is actuated to decrease the volume of the first pump chamber, the internal pressure of the first pump chamber is so increased that the valve located on the suction side of the second pump chamber is opened to pump the washing liquid from the first pump chamber to the second pump chamber.

However, if the washing liquid fed into the electromagnetic pump contains air in the form of air bubbles, then the air is compressed or expanded in association with a change in the volume of the first pump chamber, even though the plunger is actuated. This in turn results in a vapor lock situation in which a reduction in the force for opening or closing the valve located on the suction side of the second pump chamber with the discharge pressure of the electromagnetic pump is considerably reduced to a minimum discharge pressure of about 0.3 kg/cm$^2$ gauge.

Such dental washers are mainly used in prosthodontia clinics, and they make use of a heating vessel having a relatively small volume (on the order of about 400 cc at which sufficient outcomes are obtainable), since the amount of steam used for one washing may be reduced or limited. Thus, when the washing liquid is fed into the closed heating vessel, its internal pressure is so likely to rise because of its small volume so that, if the washing liquid fed into the electromagnetic pump contains air in the form of air bubbles, there is then a reduction in the difference between the pressure in the heating vessel and the discharge pressure of the electromagnetic pump, thus encountering vapor lock and difficulty in feeding the washing liquid into the heating vessel. Thus, not only is a considerable length of time needed to feed the desired amount of the washing liquid into the heating vessel, but it is also impossible to supply the washing liquid into the heating vessel, when the pressure in the heating vessel exceeds the discharge pressure of the electromagnetic pump.

In order to remove the defects of such a dental washer, there has been proposed such a steam washer unit as disclosed in Japanese Utility Model Laid-Open No. 197692/1988. This arrangement includes an air vent cock connected to a liquid supply pipeline extending between an electromagnetic pump and a check valve positioned on its discharge side. While air is expelled from within the electromagnetic pump, a washing liquid is pumped into a heating vessel by opening that air vent cock. This cock is manually opened or closed.

A problem with the dental washer of such a structure is that it needs some labor and so is inconvenient to operate. This is because when the washing liquid to be supplied contains air in the form of air bubbles, the air vent cock should be closed manually, after, while that cock is kept opened manually, the air bubble-containing washing liquid is pumped to fill a first pump chamber of the electromagnetic pump with the air bubble-free washing liquid alone, thereby recovering its discharge pressure. Another disadvantage is that when the air vent cock remains open inadvertently, a large amount of the washing liquid overflows the first pump chamber. In addition, when the first pump chamber of the electromagnetic pump is filled with the washing liquid containing air in the form of air bubbles during the operation of the dental washer, when the air vent cock remains closed inadvertently, it is impossible to pump the washing liquid into the heating vessel due to the elevated internal pressure in the heating vessel. It is then necessary to open the air vent cock manually to fill the first pump chamber of the electromagnetic pump with the washing liquid alone and thereafter close it manually. Thus, this unit is very difficult to deal with.

SUMMARY OF THE INVENTION

A primary object of this invention is to provide a dental washer assembly which successfully eliminates the above defects of the prior art and, even when a washing liquid supplied into a pipe located on the suction side of an electromagnetic pump or a first pump chamber of the electromagnetic pump contains air in the form of air bubbles, can pump the desired amount of the washing liquid into a heating vessel within a short time to generate superheated steam of a preset temperature for washing gypsum models, etc. while an operator using it does nothing special but turn on a main switch.

As a result of intensive studies made by the present inventor, it has now been found that this object is attainable if the internal pressure of a heating vessel is restored to atmospheric pressure by opening an electromagnetic valve for steam, thereby improving the relative dischargeability of an electromagnetic pump, while the air contained in a pipeline located on the suction side of the electromagnetic pump or a first pump chamber of the electromagnetic pump in the form of air bubbles is rather positively sent into the heating vessel, when there is a lowering in the discharge pressure of the electromagnetic pump because of the washing liquid to be supplied contains air in the form of air bubbles. In other words, it has been found that if there is provided a valve-closing circuit which automatically puts an electromagnetic valve for steam into an open position and actuates an electromagnetic pump upon a main switch being turned on; and automatically puts the electromagnetic valve, now open, into a closed position in response to a signal coming from a level detector means and keeping it closed upon the level of the washing liquid in the heating vessel reaching the preset upper limit, it is then possible for an operator to easily and surely pump the washing liquid into the heating vessel, the operator doing nothing but turning on a main switch.

BRIEF DESCRIPTION OF THE DRAWINGS

The dental washer according to the present invention will now be explained specifically but not exclusively with reference to the accompanying drawings, in which.

DESCRIPTION OF PREFERRED EMBODIMENTS

Figure 1:
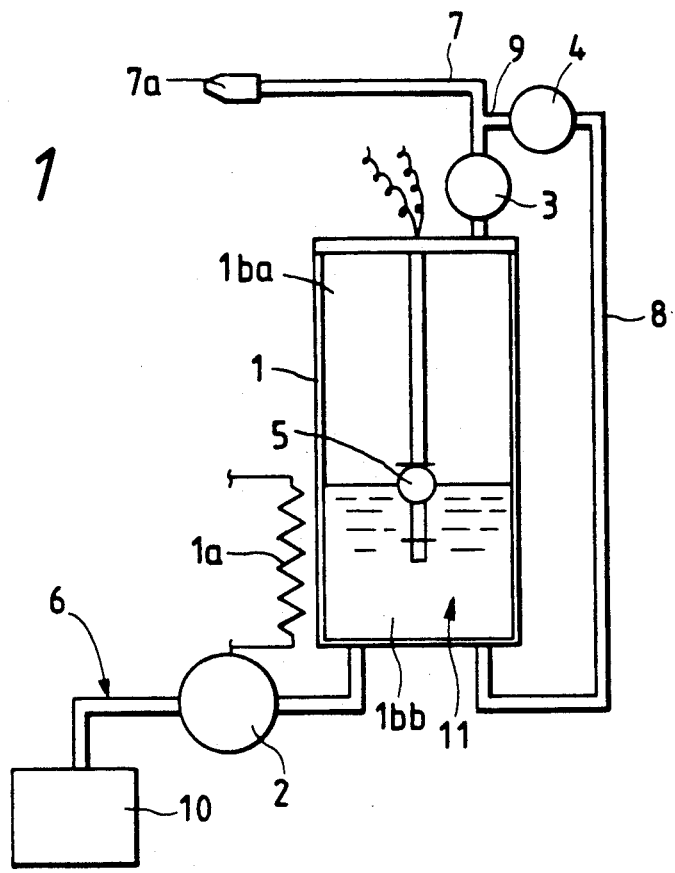
FIG. 1 is a view illustrative of the structure of one embodiment of the dental washer according to the present invention.
Figure 3:
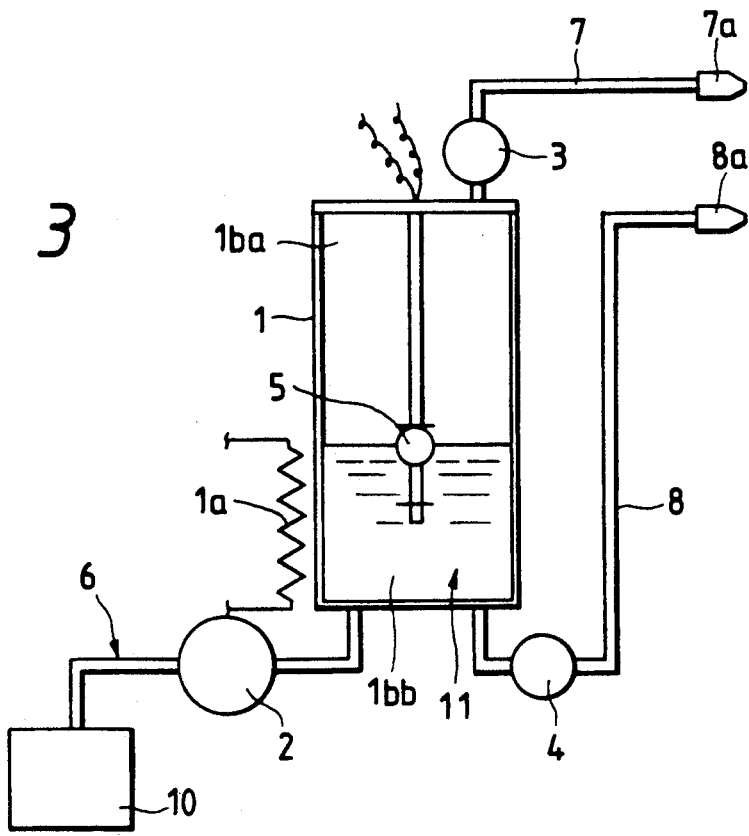
FIG. 3 is a view illustrative of the structure of another embodiment of the dental washer according to the present invention.

Referring to the drawings, reference numeral 1 stands for a heating vessel for heating a washing liquid 11 fed thereinto by means of an electrical heater 1a to generate superheated steam, and 2 denotes an electromagnetic pump located somewhere in a liquid supply pipe 6 which communicates with the heating vessel 1 and a liquid source 10 for feeding the washing liquid 11 from the liquid source 10 into the heating vessel 1. This pump 2 is stopped in response to a signal coming from a level detector means 5, such as a float switch, when the level of the washing liquid 11 in the heating vessel 1 reaches the preset upper limit, while it is actuated when the level drops to the preset lower limit. As the liquid source 10 for the washing liquid 11 which communicates with one end of the liquid supply pipe 6, use may be made of cheap tap water. It is preferred, however, that a water softener for removing calcium, magnesium, etc. contained in tap water is provided so as to prevent any clogging phenomena from occurring in the pipelines, etc. Reference numeral 3 indicates an electromagnetic valve for steam located somewhere in a steam pipe 7 which includes at one end a nozzle 7a for jetting the superheated steam from the heating vessel 1 and communicates at the other end with a superheated steam-filling region 1ba of the heating vessel 1, and 4 stands for an electromagnetic valve for boiling water, located somewhere in a boiling water pipe 8, which includes at one end a boiling water-jetting nozzle 8a and communicates at the other end with a washing liquid-storing region 1bb of the heating vessel 1, as illustrated in FIG. 3, or which communicates at one end with a junction region 9 communicating with a point in the steam pipe 7 extending between the steam-jetting nozzle 7a and the electromagnetic valve 3 and at the other end with the washing liquid-storing region 1bb of the heating vessel 1, as illustrated in FIG. 1.

The above elements are built in an electrical circuit wired as illustrated in the automatic control circuit diagram of FIG. 2, and controlled as follows.

Figure 4:
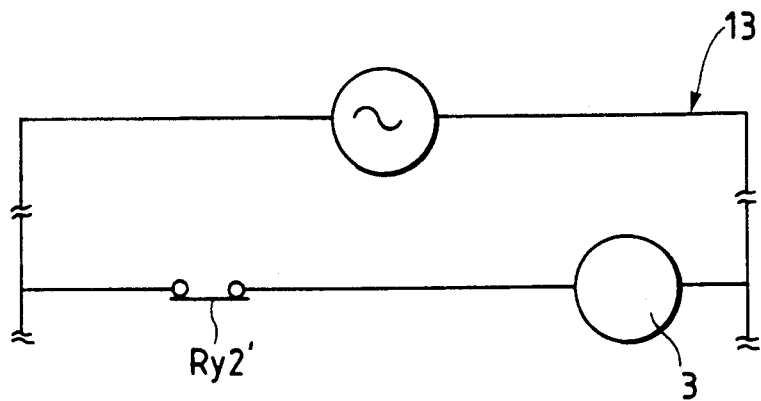
FIG. 4 is a view showing an initial open circuit of an electromagnetic valve for steam in FIG. 2.
Figure 5:
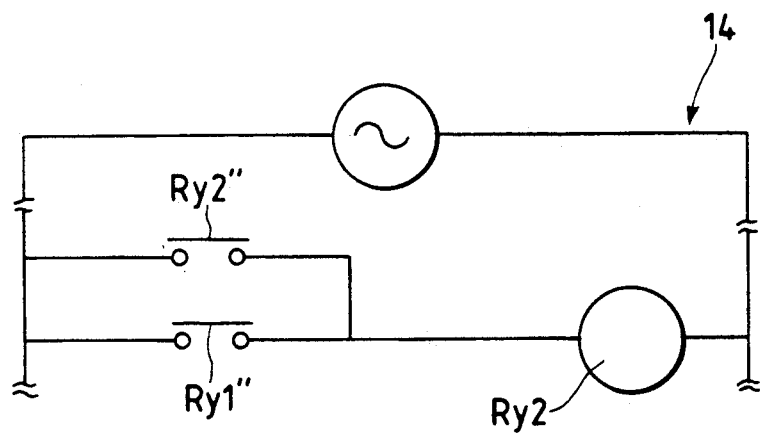
FIG. 5 is a view depicting a valve-closing circuit in FIG. 2.
Figure 6:
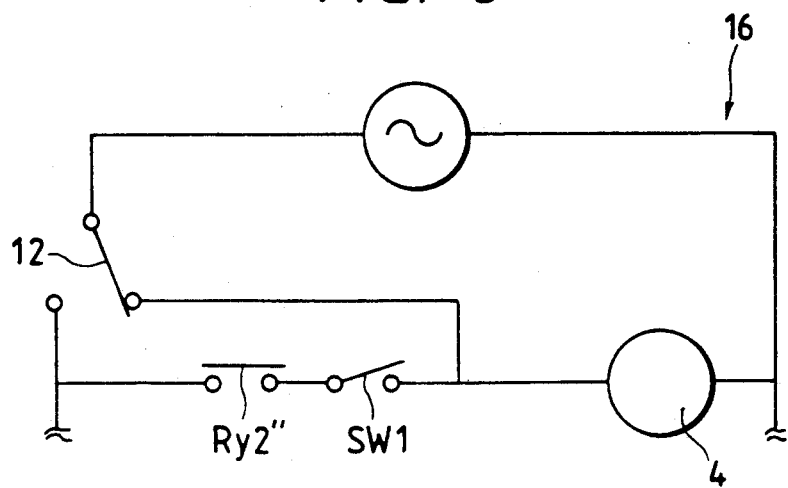
FIG. 6 is a view showing a drain circuit in FIG. 2.

Reference numeral 13, as shown in FIG. 4, stands for an initial valve-opening circuit which, upon a main switch 12 being turned on, is automatically energized to keep the electromagnetic valve 3 open. Unless a relay Ry2 to be described later is actuated, this circuit 13 closes a relay contact Ry2' adapted to open or close the electromagnetic valve 3, as shown in FIG. 4, thereby keeping the electromagnetic valve 3 open. Reference numeral 14, as shown in FIG. 5, stands for a valve-closing circuit which is actuated to close the electromagnetic valve 3, now open, in response to a signal coming from the level detector means 5 upon the level of the washing liquid 11 in the heating vessel 1 reaching the preset upper limit and keeping it closed. Unless the preset upper-limit level is detected by the level detector means 5, the valve-closing circuit 14 does not actuate a relay Ry1. Unless the relay Ry1 is actuated, this circuit keeps a relay contact Ry1" open, as depicted in FIG. 5, and keeps the relay Ry2 from actuation. Relay contacts Ry1" and Ry2" built in this circuit 14 are connected in parallel to the relay Ry2. Thus, when the level detector means 5 senses a level exceeding the preset limit, to actuates the relay Ry1, the relay contact Ry2" remains closed even though the relay Ry1 is stopped, so that the relay Ry2 remains actuated to keep the relay Ry2' of the circuit 13 open, thereby keeping the electromagnetic valve 3 closed. Reference numeral 15 denotes a manual valve-controlling switch for steam which is manually turned on or off to place the electromagnetic valve 3 remaining closed by the valve-closing circuit 14 into an open or closed position. This switch 15 is connected in parallel with the relay contact Ry2' of the initial valve-opening, circuit 13 for keeping the electromagnetic valve 3 closed when the washing liquid 11 in the heating vessel 1 reaches the preset upper-limit level after the main switch 12 is turned on. Reference numeral 16, as shown in FIG. 6, indicates a drain circuit which is actuated to keep the electromagnetic valve 4 open upon the main switch 12 being turned off. Except when the main switch 12 is turned off, the electromagnetic valve 4 is controlled into an open or closed position by a manual valve-controlling switch SW1 for boiling water, as depicted in FIGS. 2 and 6. T denotes a timer which controls the transmission of an off signal from the level detector means 5 to be transmitted after the lapse of a predetermined period of time, i.e. with a certain time lag, to stop the operation of the electrical heater 1a when the washing liquid 11 heated in the heating vessel 1 by the electrical heater 1a actuated in response to an on signal from the level detector means 5 drops to the preset lower limit. This relieves any thermal shocks resulting from electromagnetic pump 2 supplying washing liquid of normal temperature to heating vessel 1 which is at a high temperature and pressure. The electrical heater 1a is connected in series with a timer contact T' actuated by the timer T, a temperature fuse TF, a pressure switch SW2 and the relay contact Ry2" controlled by the relay Ry2.

Figure 2:
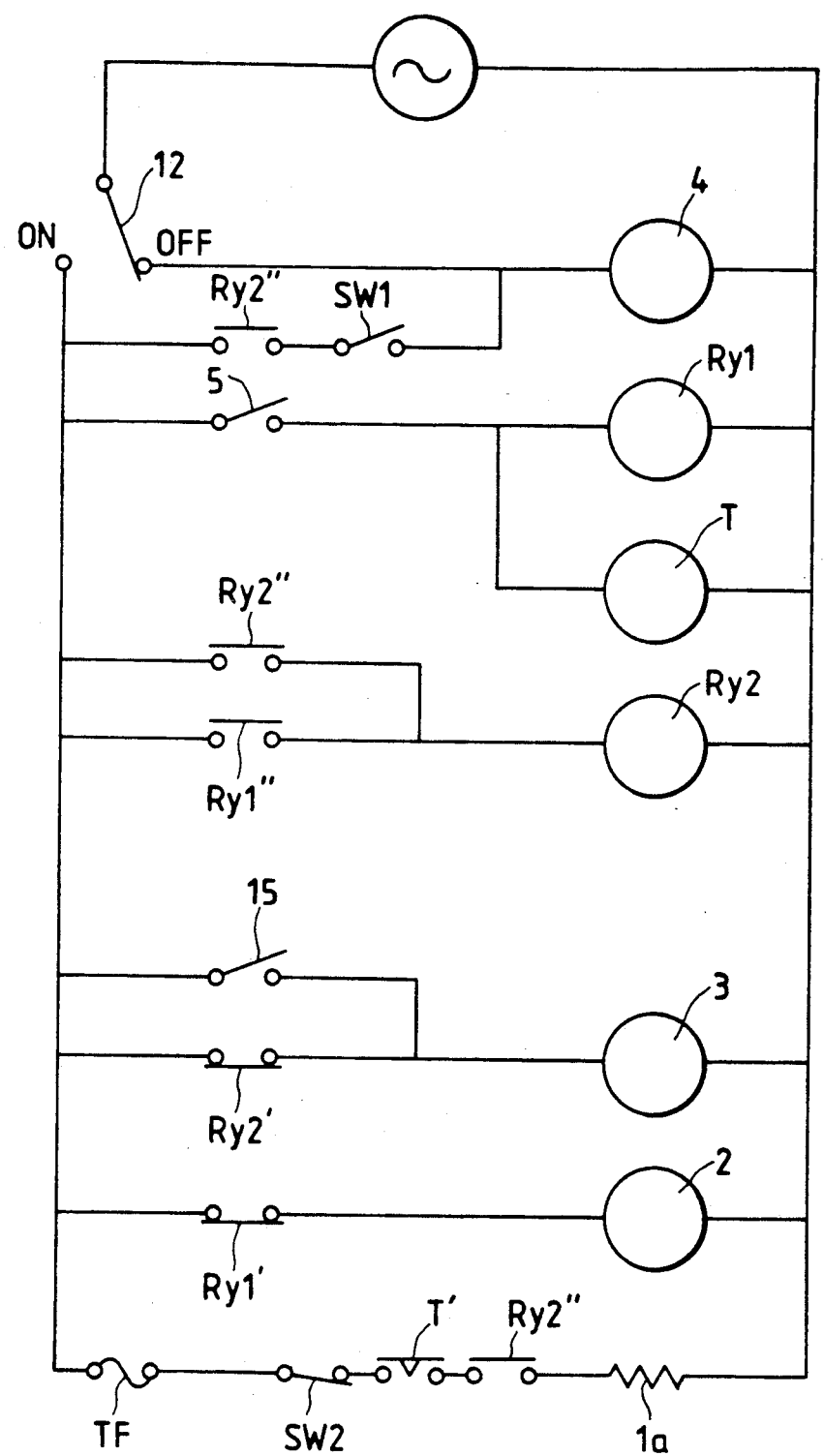
FIG. 2 is a view showing an automatic control circuit of the dental washer depicted in FIG. 1.

In the present dental washer of such a structure as mentioned above, the relay Ry1 is not actuated even when the main switch 12 is turned on, so that the relay contact Ry1" remains open, unless the washing liquid 11 in the heating vessel 1 reaches the preset upper-limit level and is detected by the level detector means 5 of the valve-closing circuit 14, as will be understood from the automatic control circuit diagram of FIG. 2. Unless the relay Ry2 is actuated to close the relay contact Ry2", the relay contact Ry2' of the relay Ry2 remains closed so that the electromagnetic valve 3 is kept open by the initial valve-opening circuit 13. Thus, the washing liquid 11 can easily be supplied into the heating vessel 1 by the electromagnetic pump 2, even when air in the form of air bubbles is present in the water supply pipe 6 or the electromagnetic pump 2. Then, when the relay Ry1 is actuated in response to a signal coming from the level detector means 5 which detects that the washing liquid 11 in the heating vessel 1 reaches the preset upper limit; the relay contact Ry1' is opened to stop the driving of the electromagnetic pump 2, so that the supply of the washing liquid 11 into the heating vessel 1 is stopped. With this, the relay contact Ry1" of the valve-closing circuit 14 is closed to keep the relay Ry2 in operation, thus the relay contact Ry2" is closed to operate the relay Ry2, while the relay contact Ry2' of the initial valve-opening circuit 13 is opened to keep the electromagnetic valve 3 closed. The relay contact Ry2" connected in series with the electrical heater 1a is also closed to pass a current through the electrical heater 1a. Then, when the internal pressure of the heating vessel 1 reaches the predetermined pressure to put the pressure switch SW2 (a pressure switch of the type which is turned off upon the upper-limit pressure being reached and turned on upon the lower-limit pressure being reached, e.g., a pressure switch SPS-8T made by Sanwa Electric Co., Ltd.) off, the washing liquid 11 is converted to superheated steam of the predetermined temperature and so can be jetted at any time. With a current supplied to the electromagnetic valve 3 remaining closed by the valve-closing circuit 14 by turning switch 15 on, the electromagnetic valve 3 is put into an open position to jet through the nozzle 7a the overheated steam in the heating vessel 1 from the superheated steam-filling region 1ba, through steam pipe 7 and electromagnetic valve 3. Where there is provided the boiling water pipe 8 in communication with the washing liquid-storing region 1bb in the heating vessel 1, the relay Ry2 is kept in operation by the valve-closing circuit 14, as already mentioned, so that the relay contact Ry2" provided in the drain circuit 16 is kept closed. Thus, with a current supplied to the electromagnetic valve 4 by turning a manual valve-controlling switch SW1 on, the electromagnetic valve 4 is held open so that the washing liquid 11 in the heating vessel 1 is supplied from the washing liquid-storing region 1bb by way of the boiling water pipe 8 and electromagnetic valve 4 to the nozzle 8a in the case of the embodiment shown in FIG. 3, from which it is jetted in a boiling state, to the nozzle 7a in the case of the embodiment shown in FIG. 1, from which it is jetted in a boiling state. Or it is jetted in the form of a mixture with the overheated steam coming through the electromagnetic valve 3 or a relatively heavy wet vapor mixed with the superheated steam and heated washing liquid 11. Upon the level of the washing liquid 11 in the heating vessel 1 reaching the preset lower limit, the relay Ry1 is stopped in response to a signal from the level detector means 5, so that the relay contact Ry1' is closed. Subsequently, the electromagnetic pump 2 is driven to supply the washing liquid 11 into the heating vessel 1 until the level of the washing liquid 11 in the heating vessel 1 reaches the preset upper limit. Where there is provided the timer T, an off signal from the level detector means 5 is transmitted to the electrical heater 1a after a certain time lag, thus making it possible to relieve thermal shocks which are caused by the electromagnetic pump 2 being actuated to supply the washing liquid 11 of normal temperature into the heating vessel 1 maintained at high temperature and pressure.

EFFECT OF THE INVENTION

According to the inventive dental washer as detailed above, the main switch is turned on when supplying the washing liquid from the liquid source to the heating vessel. Thereupon, the electromagnetic valve for steam is automatically held open by the initial valve-opening circuit, so that the electromagnetic pump is operated, while the heating vessel, to which the washing liquid is supplied, is at atmospheric pressure. Thus, even when the washing liquid on the suction side of the electromagnetic pump or in the pump chamber thereof contains air in the form of air bubbles, it is unlikely that the discharge pressure of the electromagnetic pump will drop so excessively that vapor-lock occur and the washing liquid cannot be supplied. Upon the level detector means providing a detection of the time when the level of the washing liquid in the heating vessel reaches the preset upper limit, the valve-closing circuit is actuated to hold the electromagnetic valve for steam closed. Supplying the washing liquid into the heating vessel and heating the interior of the heating vessel in a closed state can thus be carried out automatically or unattended by an operator. In addition, because the liquid supply pipe, on which the electromagnetic pump is mounted, is in communication with only the liquid source and the heating vessel with a built-in electrical circuit for automatically stopping the electromagnetic pump when the level of the washing reaches the preset upper limit, it is unlikely that the washing liquid supplied will overflow as in the case with a conventional dental washer having an air vent cock and a check valve in a water supply pipe. In consequence, the inventive washer unit can be handled so easily that the work load can be relieved and dental works can be carried out securely and surely. Further, when there is provided a boiling water pipe in communication with the washing liquid-storing region of the heating vessel, it is possible to jet not only steam but also boiling water. Still further, when this boiling water pipe is in communication with a steam pipe extending between the nozzle for steam and the electromagnetic valve for steam and there is provided a manual valve-controlling switch for boiling water which manually holds open or closed an electromagnetic valve for boiling water, located somewhere in that boiling water pipe, relatively dry steam, relatively wet steam or boiling water can be selected depending upon the state of the object to be washed. Thus, washing can be carried out more efficiently and more surely within a shorter time.

The present dental washer according to the present invention has a number of advantages and so makes a great contribution to dental fields.

What is claimed is:

1. A dental washer comprising:
   a heating vessel for heating a washing liquid by an electrical heater to generate superheated steam;
   an electromagnetic pump located on a liquid supply pipe and communicating with said heating vessel and a liquid source to supply liquid from said liquid source into said heating vessel;
   an electromagnetic valve located in a steam pipe having at its one end a nozzle for outputting steam and communicating at its other end to a superheated steam-filling region of said heating vessel;
   a level detector means for detecting a level of the washing liquid in the heating vessel, and to turn on the electrical heater when said level reaches a predetermined upper limit and to turn off the electrical heater when said level reaches a predetermined lower limit;
   an initial valve-opening circuit which is energized upon a main switch being turned on to hold said electromagnetic valve open;
   a valve-closing circuit for holding said electromagnetic valve closed in response to a signal from said level detector means indicating that the level of the washing liquid in the heating vessel reaches the predetermined upper limit and keeping it closed; and,
   a manual valve-controlling switch which can open or close said electromagnetic valve held closed by said valve-closing switch.

2. A dental washer as claimed in claim 1, further comprising a timer for transmitting an off signal from the level detector means to the electrical heater after the lapse of a predetermined period of time to turn off said heater, when the level of the washing liquid in the heating vessel reaches the predetermined lower limit.

3. A dental washer as claimed in one of claims 1 or 2, further comprising:
   an electromagnetic valve located in a boiling water pipe having at its one end a nozzle for outputting boiling water and communicating at its other end with a washing liquid-storing region of said heating vessel; and,
   a manual valve-controlling switch for holding said electromagnetic valve open or closed.

4. A dental washer as claimed in one of claims 1 or 2, further comprising:
   a boiling water pipe communicating with said steam pipe and extending between said nozzle and said electromagnetic valve, said boiling water pipe further communicating with a washing liquid-storing region of said heating vessel; and,
   a manual valve-controlling switch for holding an electromagnetic valve located in said boiling water pipe open or closed.

5. A dental washer as claimed in claim 3, further comprising a drain circuit for holding said electromagnetic valve open when the main switch is turned off.

6. A dental washer as claimed in claim 4, further comprising a drain circuit for holding said electromagnetic valve open when the main switch is turned off.

* * * * *